United States Patent
Belbachir et al.

(10) Patent No.: US 7,160,505 B2
(45) Date of Patent: Jan. 9, 2007

(54) METHOD FOR BACTERICIDAL, FUNGICIDAL, VIRUCIDAL AND INSECTICIDAL TREATMENT OF AMBIENT AIR

(75) Inventors: Hakima Belbachir, La Mure (FR); Jean Angelidis, Saint Ismier (FR)

(73) Assignee: Hightech Business Agency, La Mure (FR)

( * ) Notice: Subject to any disclaimer, the term of this patent is extended or adjusted under 35 U.S.C. 154(b) by 652 days.

(21) Appl. No.: 10/088,516

(22) PCT Filed: Jul. 31, 2001

(86) PCT No.: PCT/FR01/02506

§ 371 (c)(1),
(2), (4) Date: Aug. 19, 2002

(87) PCT Pub. No.: WO02/09777

PCT Pub. Date: Feb. 7, 2002

(65) Prior Publication Data

US 2003/0039578 A1   Feb. 27, 2003

(30) Foreign Application Priority Data

Jul. 31, 2000   (FR) .................................. 00 10064

(51) Int. Cl.
*A61L 9/00* (2006.01)

(52) U.S. Cl. .................... 422/4; 55/350.1; 239/60; 422/5; 422/120; 422/122; 424/76.2; 512/4

(58) Field of Classification Search ............... 422/122, 422/4, 120, 5; 239/60; 424/76.2; 55/350.1; 512/4

See application file for complete search history.

(56) References Cited

U.S. PATENT DOCUMENTS

| 3,547,576 | A   |   | 12/1970 | Sheikh .......................... 21/53 |
| 5,246,919 | A   |   | 9/1993 | King ............................... 512/4 |
| 5,433,923 | A   | * | 7/1995 | Wolverton et al. .......... 422/121 |
| 5,492,675 | A   | * | 2/1996 | Brizard ........................ 422/122 |
| 5,523,057 | A   | * | 6/1996 | Mazzilli ....................... 422/121 |
| 5,772,959 | A   | * | 6/1998 | Bermas ......................... 422/5 |
| 6,254,823 | B1  | * | 7/2001 | Rees ............................. 422/5 |
| 6,270,720 | B1  | * | 8/2001 | Mandish ........................ 422/4 |
| 6,680,028 | B1  | * | 1/2004 | Harris ......................... 422/122 |

FOREIGN PATENT DOCUMENTS

| FR | 2 603 806 |   | 3/1988 |
| GB | 2 251 792 |   | 7/1992 |
| GB | 2 259 858 |   | 3/1993 |
| SU | 1702111   | * | 12/1991 |
| WO | 97/35625  |   | 10/1997 |

* cited by examiner

*Primary Examiner*—Krisanne Jastrzab
(74) *Attorney, Agent, or Firm*—Jacobson Holman PLLC

(57) ABSTRACT

A method for bactericidal, fungicidal, virucidal and insecticidal treatment of ambient air includes circulating air through a permeable container having at least a treating agent therein. The treating agent is used as bactericide, fungicide, virucide and insecticide additionally to mechanical air filtering, and is distributed uniformly inside the container so as to prevent micro-organisms from developing on the container itself. The method may be applied to caloric-exchanging and air-recycling installations and appliances, and to coating elements of building surfaces.

18 Claims, 2 Drawing Sheets

Figure 1:
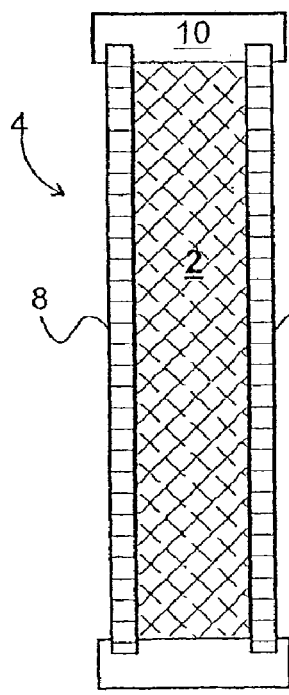

METHOD FOR BACTERICIDAL, FUNGICIDAL, VIRUCIDAL AND INSECTICIDAL TREATMENT OF AMBIENT AIR

This is a nationalization of PCT/FR01/02506 filed Jul. 31, 2001 and published in French.

TECHNICAL FIELD OF THE INVENTION

The field of the invention is air treatment, and the invention relates to a method for applying a bactericidal, fungicidal, virucidal and insecticidal treatment of ambient air, and also to a device for implementing this method and to the uses made thereof.

STATE OF THE ART

Various methods of physicochemical treatment of ambient air are known. In general, the air is drawn through a permeable container in which is placed at least one treating agent. For example, if the air treatment is a mechanical treatment aimed at removing therefrom dust in suspension, the treating agent is a filter consisting of a microperforated sheet, made of cellular or synthetic material, or of a layer of alveolate material. For example again, if the air treatment is a chemical treatment, the treating agent consists of an active agent, such as a charcoal-based agent, in order to modify the chemical composition of the air and/or to absorb toxic gases therefrom. For example, finally, if the air treatment is a physicochemical treatment, the treating agent is a source of radiation, in particular of ultraviolet radiation. It will be understood that the air may be drawn through several successive treating agents of respective nature, the containers being, for example, juxtaposed inside a common receptacle comprising an inlet for air to be treated and an outlet for treated air.

Document SU 19904786074 relates to a device for the filtering and bactericidal treatment of ambient air using crystals of sodium chloride, NaCl, and of potassium chloride, KCl. The air is then refiltered before being sterilized by radiation using a lamp.

The problem which remains to be solved in these known devices is the risk of contamination of the container in response to the mechanical filtering effect.

SUBJECT OF THE INVENTION

The aim of the present invention is to provide a method for treatment of ambient air, and for decontamination of the container, and also means for the implementation thereof within a context of domestic applications.

The method according to the present invention consists in using a treating agent which has bactericidal, fungicidal, virucidal and insecticidal effects, in addition to mechanical filtration, and in distributing the treating agent uniformly inside the container, so as to prevent the development of microorganisms on the container itself.

More particularly, the treating agent is composed of crystals of mineral salt, in particular sodium chloride (NaCl).

The treating agent may also contain elements of natural origin, in particular of plant origin, such as clove.

It will also be noted that the mineral salt crystals may advantageously be mixed with other treating agents, preferably of natural origin.

The invention also relates to a device for treating ambient air, comprising two microperforated sheets for mechanically filtering the air and a layer of bactericidal, fungicidal, virucidal and insecticidal treating agent which is distributed uniformly between said sheets so as to prevent the development of microorganisms on the walls. By virtue of this set up, the ambient air is not only treated mechanically so as to remove therefrom the particles in suspension, and biologically so as to freshen it, but is also used to carry natural substances which are beneficial to people's health, mineral salts and, secondarily, substances of plant origin in particular.

It will be understood that the container of the mineral salt crystals of the invention can, where appropriate, be juxtaposed, along the direction in which the air is drawn, or circulated, with at least one other container which contains a treating agent of another nature, in particular mechanical and/or physicochemical, so as to form an overall device for treatment of ambient air.

The method of circulating the ambient air through the salt crystals, and also the design of the container, [lacuna] unimportant as far as the scope of the invention goes and are linked to the specific use made thereof.

Thus, and according to various variants of the method of circulating the air through the salt crystals, it is drawn artificially or naturally.

According to a first variant, the circulation of air is caused artificially by ventilation. This variant in particular falls within the context of a first group of applications of the invention to calorie-exchanging devices, such as heating or refrigerating devices, air conditioners, or air-recycling appliances.

According to a second variant, the circulation of air is caused naturally, by evaporation of gas or by pressure variation for example. This variant in particular falls within the context of a second group of applications of the invention to purifying air coming from a fermentation environment, and more particularly to organic waste containers.

Thus again, and according to various variants of the container, in particular corresponding to the various above-mentioned methods for circulating the air through the salt crystals, these crystals may be contained inside a permeable case maintained on a support, or be contained in a flexible net closed up on itself to form a sack or be contained between the walls of a double-walled flexible container.

According to a first variant of the container, which in particular corresponds to the first group of abovementioned applications, the case, or alternately the net, is either interchangeable or organized so as to allow the crystals to be replaced. Moreover, the case, or alternately the net, is, where appropriate, placed inside a receptacle comprising an inlet for air to be treated and an outlet for treated air. It will be understood that the container, case or alternately net, is, if need be, juxtaposed with at least one similar container of a mechanical, chemical or physicochemical treating agent of the various types mentioned above.

According to a second variant of the container, corresponding to the second group of above mentioned applications, the double-walled container is, for example, closed up on itself so as to also form a sack intended to contain waste, in particular household waste. For example again, the double-walled container is arranged as a sheet for covering a fermentable material, for a landfill pit or transformation container for organic waste in particular.

SUMMARIZED DESCRIPTION OF THE DRAWINGS

Figure 2:
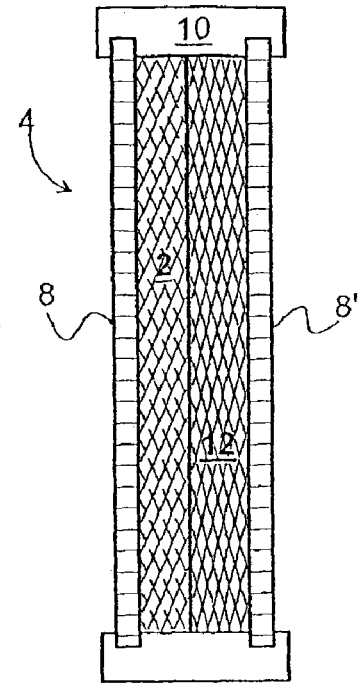
Figure 3:
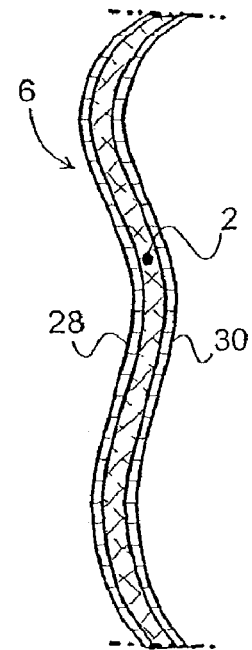
Figure 4:
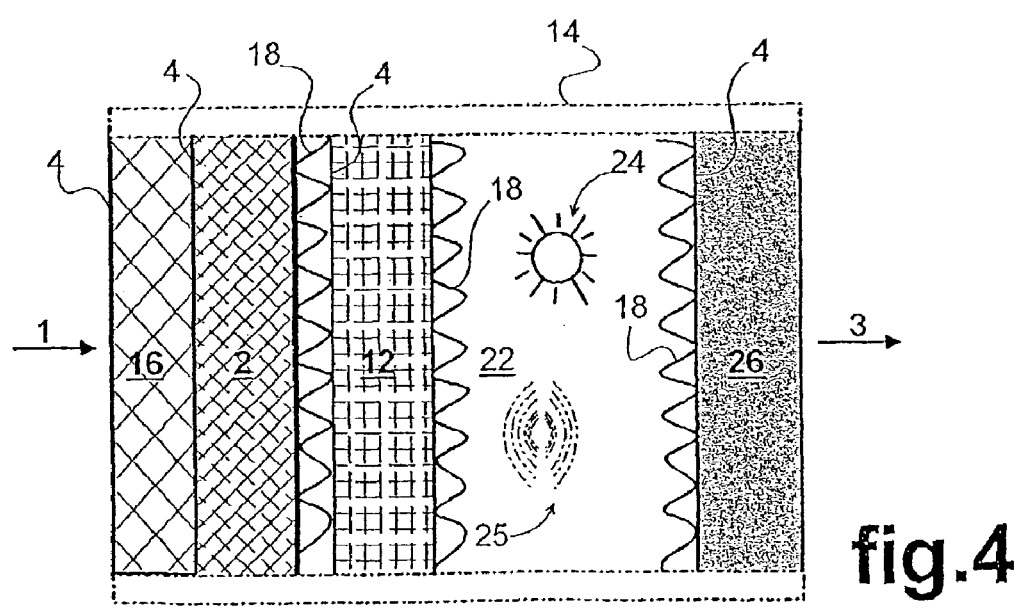

The present invention will be more clearly understood, and details which are a product thereof will become apparent, in the description which will be made up of preferred embodiments and types of application thereof, in relation to the figures on the attached plates, in which:

FIG. 1 to FIG. 3 are diagrammatical representations of various respective embodiments of a device for treatment of ambient air, which implements a method of the invention, FIG. 4 is a diagrammatical representation of a device for treatment of ambient air according to a particular type of application of a method of the invention, which uses various treating agents of respective nature, FIG. 5 to FIG. 9 are diagrams illustrating various examples of applications of the method for treatment of ambient air provided by the invention.

On FIG. 1 to FIG. 3, a device for bactericidal, fungicidal and/or insecticidal treatment of ambient air uses a treating agent 2 based on mineral salt crystals. In the various examples of the preparation illustrated, the crystals 2 are uniformly distributed inside a permeable container, such as 4 or 6, so as to prevent the development of microorganisms on the container itself.

DESCRIPTION OF PREFERENTIAL EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

On FIG. 1 and FIG. 2, the container 4 consists of two microperforated sheets 8, 8' of synthetic or natural origin, supported by a frame 10. It will be noted that the frame 10 preferably comprises an opening, not represented on the figures, which makes it possible to introduce the salt crystals between the two sheets 8, 8', or even to replace them after prolonged use. This set up is such that the container 4 is arranged in the form of a cassette of treating product 2, which can be supported by a receptacle in such a way that it can be removed, with a view to it being interchangeable.

It will be noted on FIG. 1, that the container 4 receives only salt crystals 2, whereas, on FIG. 2, the container 4 receives a layer of salt crystals 2 and a layer of treating agent of plant origin 12. According to an embodiment not represented on the figures, the salt crystals 2 and the treating agents of plant origin 12 are mixed.

Referring more particularly to FIG. 4, a device for overall treatment of air comprises a receptacle 14 with several compartments, which each house, in a removable manner, a container 4 of a treating agent of respective nature and/or origin.

Such a device preferably comprises at least any one of the following successive treating agents:

a layer of foam 16, such as natural or synthetic cotton wool, for a first crude, mechanical filtration of the polluted air 1, a layer of mineral salt crystals 2 for bactericidal, virucidal and/or fungicidal treatment of the air, a fine mechanical filter 18, such as a filter made of paper or of fabric, a layer of specific fragmented plants 12, such as thyme and/or cloves, to supplement the bactericidal and/or fungicidal and/or insecticidal action of the mineral salt crystals 2, and/or to diffuse a fragrance into the ambient air treated, and/or to provide an effect which is beneficial to people's health, concomitantly with the medicinal effects provided by the mineral salts 2, a fine mechanical filter 18 of the above-mentioned type, a compartment 22 for treatment of air by radiation, such as by ultraviolet rays 24 and/or by magnetic waves 25 and/or by sound waves, for germicidal treatment of the air, a fine mechanical filter 18 of the abovementioned type, a layer of active charcoal 26 and/or of natural wool, and/or of rare-earth metals, in order, optionally, to absorb toxic gases.

It will be understood that the various treating agents 16, 2, 12 and 26 are housed in respective containers which are similar, with a view to them being interchangeable or being removed depending on the air treatment(s) desired by the user.

Figure 9:
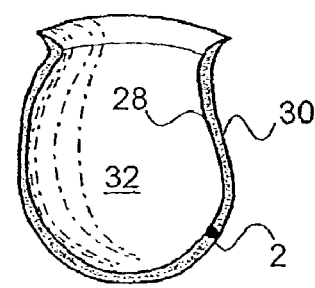

On FIG. 3, the container 6 consists of a double-wall, 28 and 30, microperforated flexible sheet for the purpose, for example of making a sack for household waste 32, such as that illustrated in FIG. 9.

On FIG. 5 to FIG. 8, a device using the method of the invention also comprises means 34 for circulating the air to be treated through at least one treating agent by ventilation, and more particularly through at least one agent based on salt crystals 2.

Figure 5:
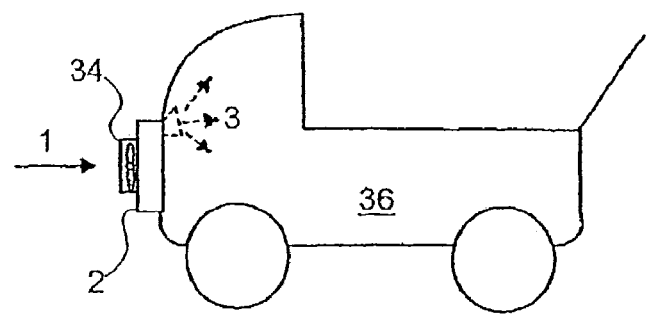

On FIG. 5, the method of the invention is applied to a child's pram 36. Similar applications will be noted, such as the passenger compartment of a vehicle or a safety hat.

Figure 6:
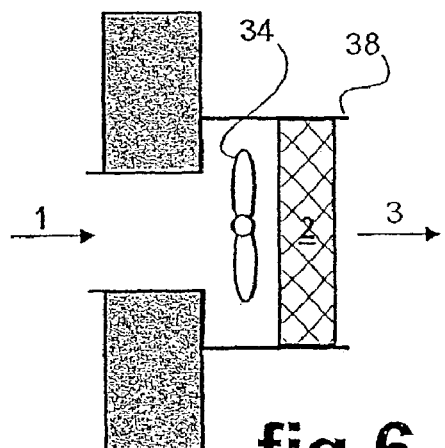
Figure 7:
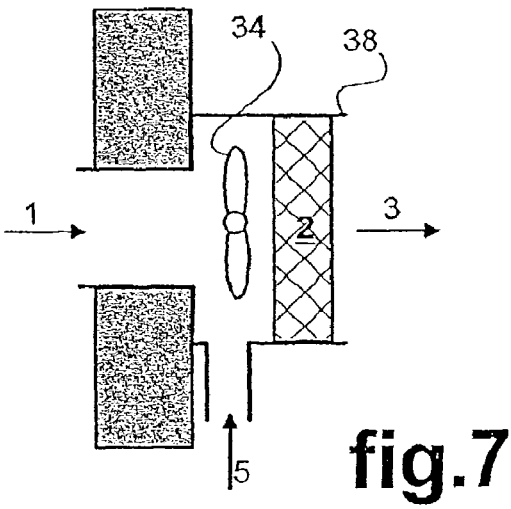

On FIGS. 6 and 7, the method of the invention is applied to calorie-exchanging appliances or installations which comprise an air ventilation circuit 38, such as air conditioners, radiators or refrigerators (FIG. 6), or air-recycling installations or appliances (FIG. 7). It will be noted that, according to this last application, the device may comprise not only an inlet for polluted air 1, but also a secondary inlet for outside air 5.

Figure 8:
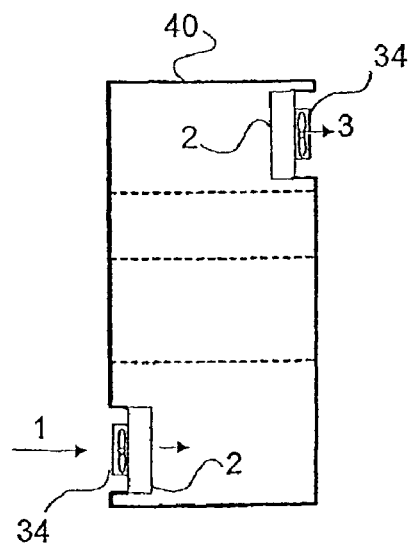

On FIG. 8, the method of the invention is applied to freshening closed environments, in particular shoe cupboards 40, cold rooms, refrigerating appliances, baby implements, etc.

An application of the invention, not represented in the figures, will also be found in the construction field, the invention being applied to elements for coating a surface, such as a floor, wall or ceiling, so as to limit the development of bacteria or fungi. According to this application, the container of salt crystals is, for example, arranged in the form of a double-walled panel or film.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for treating ambient air, comprising:
drawing in or circulating the air through a permeable container in which is placed a treating agent that includes crystals of a mineral salt and fragmented elements of plant origin selected from the group consisting of clove, thyme and both clove and thyme;

mechanically filtering said air while said treating agent concurrently acts as a bactericide, fungicide, virucide and insecticide; and distributing said treating agent with substantial uniformity inside said container so as to prevent the development of microorganisms on the container itself.

2. The method of claim 1, wherein said crystals of mineral salt and said fragmented elements of plant origin are mixed.

3. The method of claim 1, wherein said crystals of mineral salt and said fragmented elements of plant origin are in separate layers.

4. The method of claim 1, wherein the mineral salt is sodium chloride.

5. A permeable device for treating ambient air by drawing in or circulating the air through said device, comprising:
a container including two microperforated sheets for mechanical filtration of the air; and
a layer of bactericidal, fungicidal, virucidal, and insecticidal treating agent including crystals of mineral salt and fragmented elements of plant origin selected from the group consisting of clove, thyme and both clove and thyme, said layer being distributed with substantial uniformity between said sheets so as to prevent the development of microorganisms on surfaces of said container.

6. The device of claim 5, wherein the container includes a case, a net and a double-walled flexible container.

7. The device of claim 5, further comprising a component for circulating air through the container by ventilation.

8. The device of claim 5, wherein said crystals of mineral salt and said fragmented elements of plant origin are mixed.

9. The device of claim 5, wherein said crystals of mineral salt and said fragmented elements of plant origin are in separate layers.

10. The device of claim 5, further comprising at least one of the following successive treating agents:
a layer of foam for a first mechanical filtration;
a first fine mechanical filter;
a compartment for treatment of air by radiation; and
a layer of active charcoal.

11. The device of claim 5, wherein said layer of bactericidal, fungicidal, virucidal, and insecticidal treating agent includes the following successive treating agents:
a layer of foam for a first mechanical filtration;
a layer of said mineral salt crystals and fragmented elements of plant origin selected from the group consisting of clove, thyme and both clove and thyme adjacent said foam layer;
a first fine mechanical filter adjacent said layer of mineral salt crystals and fragmented plant elements;
a compartment for treatment of air by radiation adjacent said first fine mechanical filter;
a second fine mechanical filter adjacent said compartment; and
a layer of active charcoal adjacent said second fine mechanical filter.

12. The method of claim 1, wherein said air is provided to or received from a calorie-exchanging device selected from the group of devices consisting of air conditioners, heating appliances, refrigerating appliances, and ventilation and air-recycling appliances.

13. The method of claim 1, wherein the air is provided by an organic waste container selected from the group of containers consisting of household waste sacks, landfill pits for fermentable material, and transformation containers for organic waste.

14. A method for treating ambient air using a container having a plurality of layers, comprising the steps in the following order of:
drawing in or circulating the air into said container through a layer of foam for a first mechanical filtration;
drawing in or circulating the air through a treating agent layer of mineral salt crystals and fragmented plant elements selected from the group consisting of clove, thyme and both clove and thyme adjacent said foam layer, said treating agent layer concurrently acting as a bactericide, fungicide, virucide and insecticide and being distributed substantially uniformly across said container so as to prevent the development of microorganisms on the container itself;
drawing in or circulating the air through a first fine mechanical filter adjacent said layer of mineral salt crystals and fragmented plant elements; and
drawing in or circulating the air through a compartment for treatment of air by radiation adjacent said first fine mechanical filter.

15. The method of claim 14, further comprising after the step of drawing in or circulating the air through said compartment, the steps in the following order of:
drawing in or circulating the air through a second fine mechanical filter adjacent said compartment; and
drawing in or circulating the air through a layer of toxic gas-absorbing material adjacent said second fine mechanical filter to exit said container.

16. The method of claim 15, wherein said layer of toxic gas-absorbing material is selected from the group consisting of active charcoal, natural wool and rare-earth metals.

17. The method of claim 14, wherein said step of drawing in or circulating the air through a treating agent layer includes:
drawing in or circulating the air through a layer of mineral salt crystals;
drawing in or circulating the air through a second fine mechanical filter adjacent said layer of mineral salt crystals; and
drawing in or circulating the air through a layer of fragmented plant elements selected from the group consisting of clove, thyme and both clove and thyme adjacent said second fine mechanical filter.

18. The method of claim 17, further comprising after the step of drawing in or circulating the air through said compartment, the steps in the following order of:
drawing in or circulating the air through a third fine mechanical filter adjacent said compartment; and
drawing in or circulating the air through a layer of toxic gas-absorbing material adjacent said third fine mechanical filter to exit said container.

* * * * *